US009214095B2

(12) United States Patent
Kubota et al.

(10) Patent No.: US 9,214,095 B2
(45) Date of Patent: Dec. 15, 2015

(54) SURGICAL SIMULATION MODEL GENERATING METHOD, SURGICAL SIMULATION METHOD, AND SURGICAL SIMULATOR

(75) Inventors: Yoshinobu Kubota, Yokohama (JP);
Kazuhide Makiyama, Yokohama (JP);
Takaaki Kikukawa, Kamakura (JP);
Manabu Nagasaka, Kamakura (JP);
Hideo Sakamoto, Kamakura (JP);
Masato Ogata, Kamakura (JP)

(73) Assignee: MITSUBISHI PRECISION CO., LTD., Koto-Ku, Tokyo (JP)

( * ) Notice: Subject to any disclaimer, the term of this patent is extended or adjusted under 35 U.S.C. 154(b) by 852 days.

(21) Appl. No.: 13/376,697

(22) PCT Filed: Jun. 4, 2010

(86) PCT No.: PCT/JP2010/059887
§ 371 (c)(1),
(2), (4) Date: Dec. 7, 2011

(87) PCT Pub. No.: WO2010/143699
PCT Pub. Date: Dec. 16, 2010

(65) Prior Publication Data
US 2012/0081367 A1  Apr. 5, 2012

(30) Foreign Application Priority Data

Jun. 8, 2009 (JP) .................................. 2009-136898

(51) Int. Cl.
*G09B 23/28* (2006.01)
*G06T 17/20* (2006.01)
*A61B 19/00* (2006.01)

(52) U.S. Cl.
CPC .............. *G09B 23/285* (2013.01); *G06T 17/20* (2013.01); *A61B 2019/505* (2013.01)

(58) Field of Classification Search
CPC ......... G06T 17/00; G06T 17/20; G06T 19/00; G06T 2210/41; G06F 17/5018
USPC ........................................................ 345/419
See application file for complete search history.

(56) References Cited

U.S. PATENT DOCUMENTS 5,956,040 A   9/1999  Asano et al.
6,498,607 B1  12/2002 Pfister et al.
(Continued)

FOREIGN PATENT DOCUMENTS

JP   10-111958 A    4/1998
JP   2000-222601 A  8/2000
(Continued)

OTHER PUBLICATIONS

Picinbono, Guillaume, et al. "Improving realism of a surgery simulator: linear anisotropic elasticity, complex interactions and force extrapolation." The Journal of Visualization and Computer Animation 13.3 (2002): 147-167.*

(Continued)

*Primary Examiner* — Xiao Wu
*Assistant Examiner* — Scott E Sonners
(74) *Attorney, Agent, or Firm* — Buchanan Ingersoll & Rooney PC

(57) ABSTRACT

A surgical simulation model generating method includes: a first process in which a computing unit acquires geometrical information of an organ from a medical image stored in a storage unit, including an image of the organ, and generates volume data for the organ; a second process in which, after the first process, the computing unit forms nodal points by meshing the organ represented by the generated volume data; a third process in which the computing unit generates a simulated membrane that covers the organ represented by the volume data meshed in the second process; and a fourth process in which the computing unit generates a simulated organ by drawing an imaginary line so as to extend from each nodal point formed on a surface of the organ represented by the volume data meshed in the second process in a direction that intersects the simulated membrane and thereby forming a membrane nodal point at a point where the imaginary line intersects the simulated membrane generated in the third process, and by arranging on each imaginary line an imaginary inter-membrane spring that connects between the nodal point formed on the surface of the organ and the membrane nodal point, while also arranging an in-plane spring that connects between adjacent membrane nodal points on the simulated membrane.

4 Claims, 10 Drawing Sheets

(56) References Cited

U.S. PATENT DOCUMENTS

| | | | |
|---|---|---|---|
| 6,714,901 B1 * | 3/2004 | Cotin et al. | 703/7 |
| 2010/0063788 A1 * | 3/2010 | Brown et al. | 703/6 |
| 2010/0178644 A1 * | 7/2010 | Meglan et al. | 434/267 |

FOREIGN PATENT DOCUMENTS

| | | |
|---|---|---|
| JP | 4117949 B2 | 5/2008 |
| JP | 4117954 B2 | 5/2008 |
| JP | 2008-134373 A | 6/2008 |
| JP | 2008-171135 A | 7/2008 |
| JP | 4155637 B2 | 7/2008 |
| JP | 2008-292534 A | 12/2008 |
| JP | 4290312 B2 | 4/2009 |

OTHER PUBLICATIONS

International Search Report (PCT/ISA/210) issued on Jul. 20, 2010, by Japanese Patent Office as the International Searching Authority for International Application No. PCT/JP2010/059887.

* cited by examiner

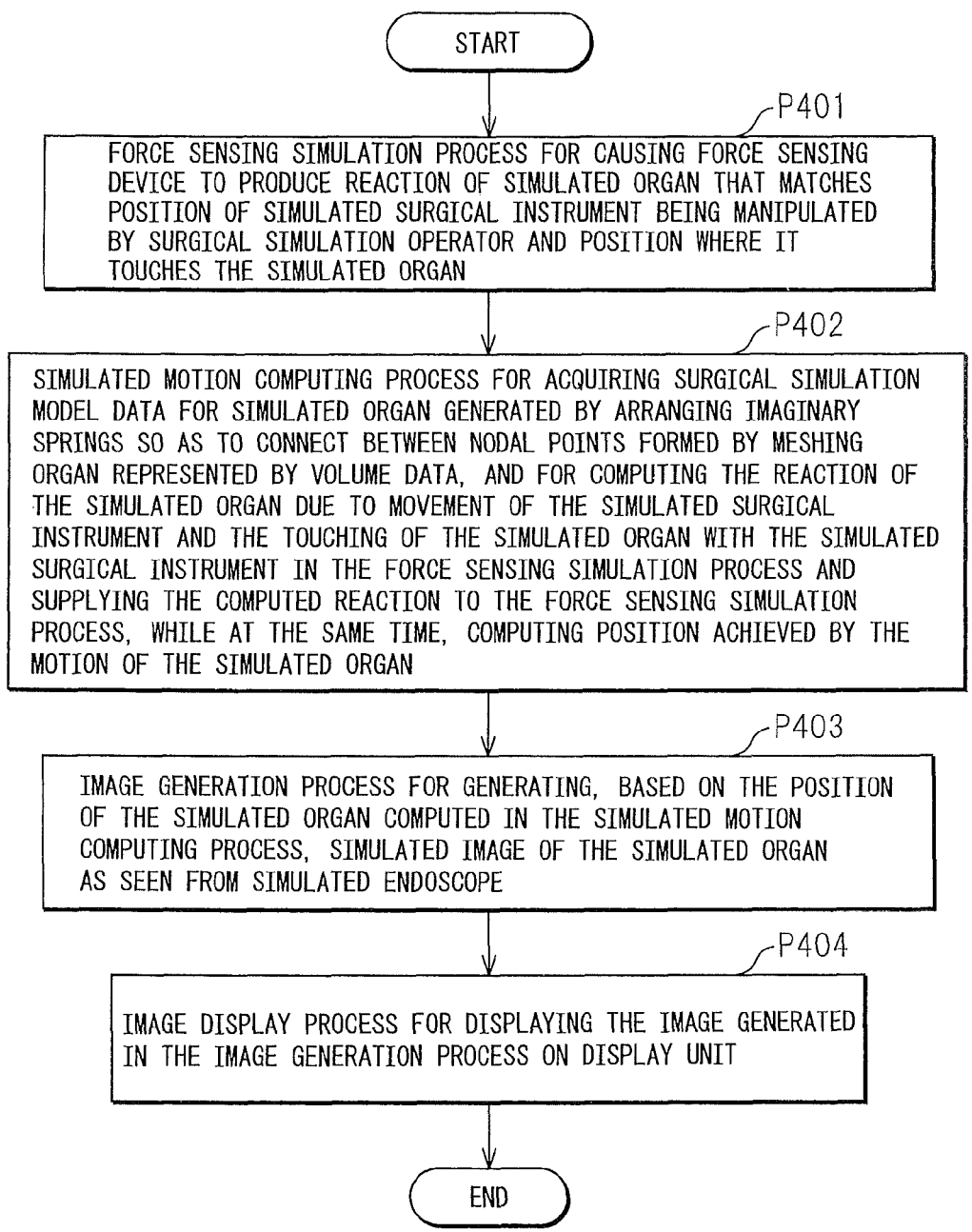

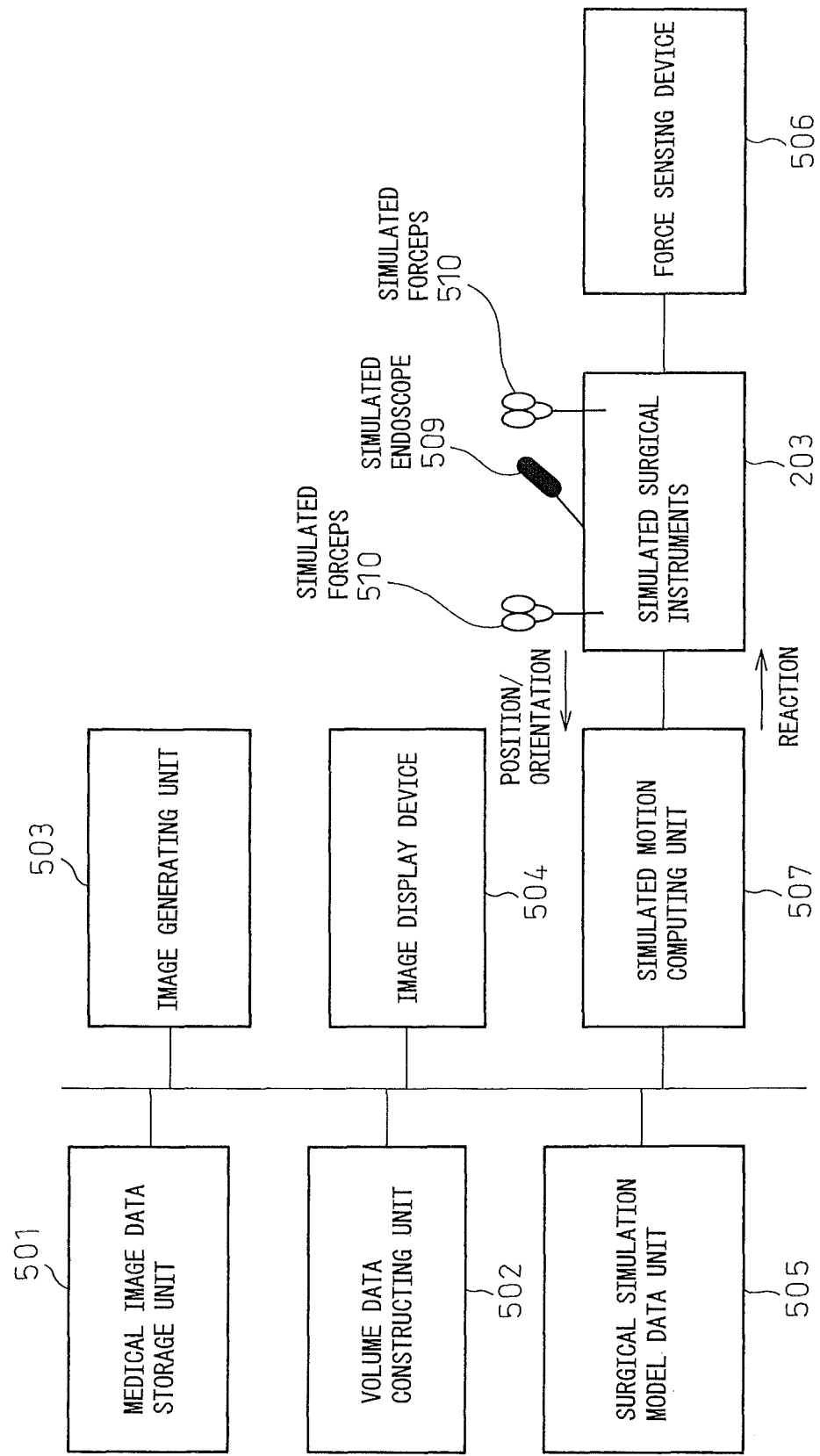

ESTIMATION OF STIFFNESS MATRIX BY PIECEWISE METHOD

SURGICAL SIMULATION MODEL GENERATING METHOD, SURGICAL SIMULATION METHOD, AND SURGICAL SIMULATOR

TECHNICAL FIELD

The present invention relates to a method for generating a surgical simulation model used when conducting a surgical simulation before performing a surgical operation using an endoscope, and also relates to a surgical simulation method and a surgical simulator.

BACKGROUND ART

With advances in medical technology and medical instruments, many abdominal surgical operations are being performed using a laparoscope. Since laparoscopic surgery is performed by viewing a three-dimensional object displayed on a two-dimensional image display device, training is indispensable for acquiring of the required skill. In actual laparoscopic surgery, the surgery must be planned so as to match each individual patient because the number of blood vessels, the positions of the blood vessels, and the positional relationship of organs, for example, the position and size of a tumor, differ from patient to patient.

For this purpose, it may be appropriate to perform, prior to surgery, a surgical simulation based on information acquired of each individual patient.

To acquire information of each individual patient, it is common to use medical image data such as CT or MRI data, but images of the membrane tissues surrounding the organ to be operated on cannot be captured by such means. Because of the inability to recognize such membrane tissues, there arises the problem that the membrane tissues cannot be modeled. A model that does not incorporate membrane tissues is unsuitable for use in a preoperative simulation. On the other hand, to compute the motion of an organ model at high speed, the physical and dynamic conditions of the model of the organ to be operated on may be set linearly. However, in this case, the deformation of the organ model would greatly differ from the actual deformation, rendering such a model unsatisfactory for use in a preoperative simulation.

Further, such a surgical simulator is equipped with a force sensing device that produces the reaction of a simulated organ that matches the position of the simulated surgical instrument being manipulated by the surgical simulation operator and the position where it touches the simulated organ. However, it is not common to compute the reaction of the simulated organ and supply the computed reaction to the force sensing device, while at the same time, computing in real time the position achieved by the motion of the simulated organ.

Further, in a prior art surgical simulation model of a simulated organ that uses a finite-element method, volume data for an organ, for example, is meshed to generate a simulated organ segmented into a plurality of tetrahedrons. Then, a stiffness matrix that describes the dynamic property of the simulated organ is generated by applying Young's modulus or Poisson's ratio or the like as physical values to the tetrahedrons. Then, the motion equation of the simulated organ that uses the stiffness matrix is solved by numerical computation, thereby simulating the motion of the simulated organ.

However, since it takes a finite time to complete the numerical computation of the motion equation that uses such a stiffness matrix, it has not been possible to compute the motion of the simulated organ in real time. Furthermore, the computation using the prior art stiffness matrix has had the problem that the computation may diverge.

PRIOR ART DOCUMENTS

Patent Documents

Patent Document 1: Japanese Patent No. 4155637
Patent Document 2: Japanese Patent No. 4117949
Patent Document 3: Japanese Patent No. 4117954
Patent Document 3: Japanese Patent No. 4290312

SUMMARY OF THE INVENTION

Problem to be Solved by the Invention

The problem to be solved by the invention is to provide a simulation model generating method, a surgical simulation method, and a surgical simulator that can compute the motion of a simulated organ in real time.

Means for Solving the Problem

The surgical simulation model generating method according to the present invention includes: a first process in which a computing unit acquires geometrical information of an organ from a medical image stored in a storage unit, including an image of the organ, and generates volume data for the organ; a second process in which, after the first process, the computing unit forms nodal points by meshing the organ represented by the generated volume data; a third process in which the computing unit generates a simulated membrane that covers the organ represented by the volume data meshed in the second process; and a fourth process in which the computing unit generates a simulated organ by drawing an imaginary line so as to extend from each nodal point formed on a surface of the organ represented by the volume data meshed in the second process in a direction that intersects the simulated membrane and thereby forming a membrane nodal point at a point where the imaginary line intersects the simulated membrane generated in the third process, and by arranging on each imaginary line an imaginary inter-membrane spring that connects between the nodal point formed on the surface of the organ and the membrane nodal point, while also arranging an in-plane spring that connects between adjacent membrane nodal points on the simulated membrane.

Another surgical simulation model generating method according to the present invention includes: a first process in which a computing unit acquires geometrical information of an organ from a medical image stored in a storage unit, including an image of the organ, and generates volume data for the organ; a second process in which, after the first process, the computing unit forms nodal points by meshing the organ represented by the generated volume data; and a third process in which the computing unit generates a simulated organ by arranging an imaginary spring so as to connect between each of the nodal points on the organ represented by the meshed volume data.

A surgical simulation method according to the present invention includes: a force sensing simulation process in which a computing unit causes a force sensing device to produce reaction of a simulated organ that matches the position of a simulated surgical instrument being manipulated by a surgical simulation operator and the position where the simulated surgical instrument touches the simulated organ; a simulated motion computing process in which the computing unit acquires, from a storage unit, surgical simulation model data for a simulated organ having an organ represented by meshed volume data and a simulated membrane covering the organ represented by the meshed volume data, the simulated organ being generated by drawing an imaginary line so as to extend from each nodal point formed on a surface of the organ represented by the meshed volume data in a direction that intersects the simulated membrane and thereby forming a membrane nodal point at a point where the imaginary line intersects the simulated membrane, and by arranging on each imaginary line an imaginary inter-membrane spring that connects between the nodal point formed on the surface of the organ and the membrane nodal point, while also arranging an in-plane spring that connects between adjacent membrane nodal points on the simulated membrane, and the computing unit then computes the reaction of the simulated organ due to a movement of the simulated surgical instrument and the touching of the simulated organ with the simulated surgical instrument in the force sensing simulation process, and supplies the computed reaction to the force sensing simulation process, while at the same time, computing the position achieved by the motion of the simulated organ; an image generation process in which the computing unit generates, based on the position of the simulated organ computed in the simulated motion computing process, a simulated image of the simulated organ as seen from a simulated endoscope; and an image display process in which the computing unit displays the image generated in the image generation process on a display unit.

Another surgical simulation method according to the present invention includes: a force sensing simulation process in which a computing unit causes a force sensing device to produce reaction of a simulated organ that matches the position of a simulated surgical instrument being manipulated by a surgical simulation operator and the position where the simulated surgical instrument touches the simulated organ; a simulated motion computing process in which the computing unit acquires, from a storage unit, surgical simulation model data for a simulated organ generated by arranging an imaginary spring so as to connect between each nodal point formed by meshing an organ represented by volume data, computes the reaction of the simulated organ due to a movement of the simulated surgical instrument and the touching of the simulated organ with the simulated surgical instrument in the force sensing simulation process, and supplies the computed reaction to the force sensing simulation process, while at the same time, computing the position achieved by the motion of the simulated organ; an image generation process in which the computing unit generates, based on the position of the simulated organ computed in the simulated motion computing process, a simulated image of the simulated organ as seen from a simulated endoscope; and an image display process in which the computing unit displays the image generated in the image generation process on a display unit.

A surgical simulator according to the present invention includes: a surgical simulation model data unit which stores surgical simulation model data for a simulated organ having an organ represented by meshed volume data and a simulated membrane covering the organ represented by the meshed volume data, the surgical simulation model data being generated by drawing an imaginary line so as to extend from each nodal point formed on a surface of the organ represented by the meshed volume data in a direction that intersects the simulated membrane and thereby forming a membrane nodal point at a point where the imaginary line intersects the simulated membrane, and by arranging on each imaginary line an imaginary inter-membrane spring that connects between the nodal point formed on the surface of the organ and the membrane nodal point, while also arranging an in-plane spring that connects between adjacent membrane nodal points on the simulated membrane; a force sensing device which produces the reaction of the simulated organ that matches the position of a simulated surgical instrument being manipulated by a surgical simulation operator and the position where the simulated surgical instrument touches the simulated organ; a simulated motion computing unit which acquires the surgical simulation model data from the surgical simulation model data unit, computes the reaction of the simulated organ due to a movement of the simulated surgical instrument and the touching of the simulated organ with the simulated surgical instrument at the force sensing device, and supplies the computed reaction to the force sensing device, while at the same time, computing the position achieved by the motion of the simulated organ; an image generating unit which generates, based on the position of the simulated organ computed by the simulated motion computing unit, a simulated image of the simulated organ as seen from a simulated endoscope; and an image display unit which displays the image generated by the image generating unit.

Another surgical simulator according to the present invention includes: a surgical simulation model data unit which stores surgical simulation model data for a simulated organ generated by arranging an imaginary spring so as to connect between each nodal point formed by meshing an organ represented by volume data; a force sensing device which produces the reaction of the simulated organ that matches the position of a simulated surgical instrument being manipulated by a surgical simulation operator and the position where the simulated surgical instrument touches the simulated organ; a simulated motion computing unit which acquires the surgical simulation model data from the surgical simulation model data unit, computes the reaction of the simulated organ due to a movement of the simulated surgical instrument and the touching of the simulated organ with the simulated surgical instrument at the force sensing device, and supplies the computed reaction to the force sensing device, while at the same time, computing the position achieved by the motion of the simulated organ; an image generating unit which generates, based on the position of the simulated organ computed by the simulated motion computing unit, a simulated image of the simulated organ as seen from a simulated endoscope; and an image display unit which displays the image generated by the image generating unit.

Advantageous Effect of the Invention

According to the simulation model generating method, surgical simulation method, and surgical simulator of the invention described above, the position achieved by the motion of the simulated organ can be computed in real time.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

FIG. 4 is a flow diagram for explaining a second embodiment of a surgical simulation method.

FIG. 5A is a functional block diagram for explaining an embodiment of a surgical simulator.

MODES FOR CARRYING OUT THE INVENTION

Figure 1:
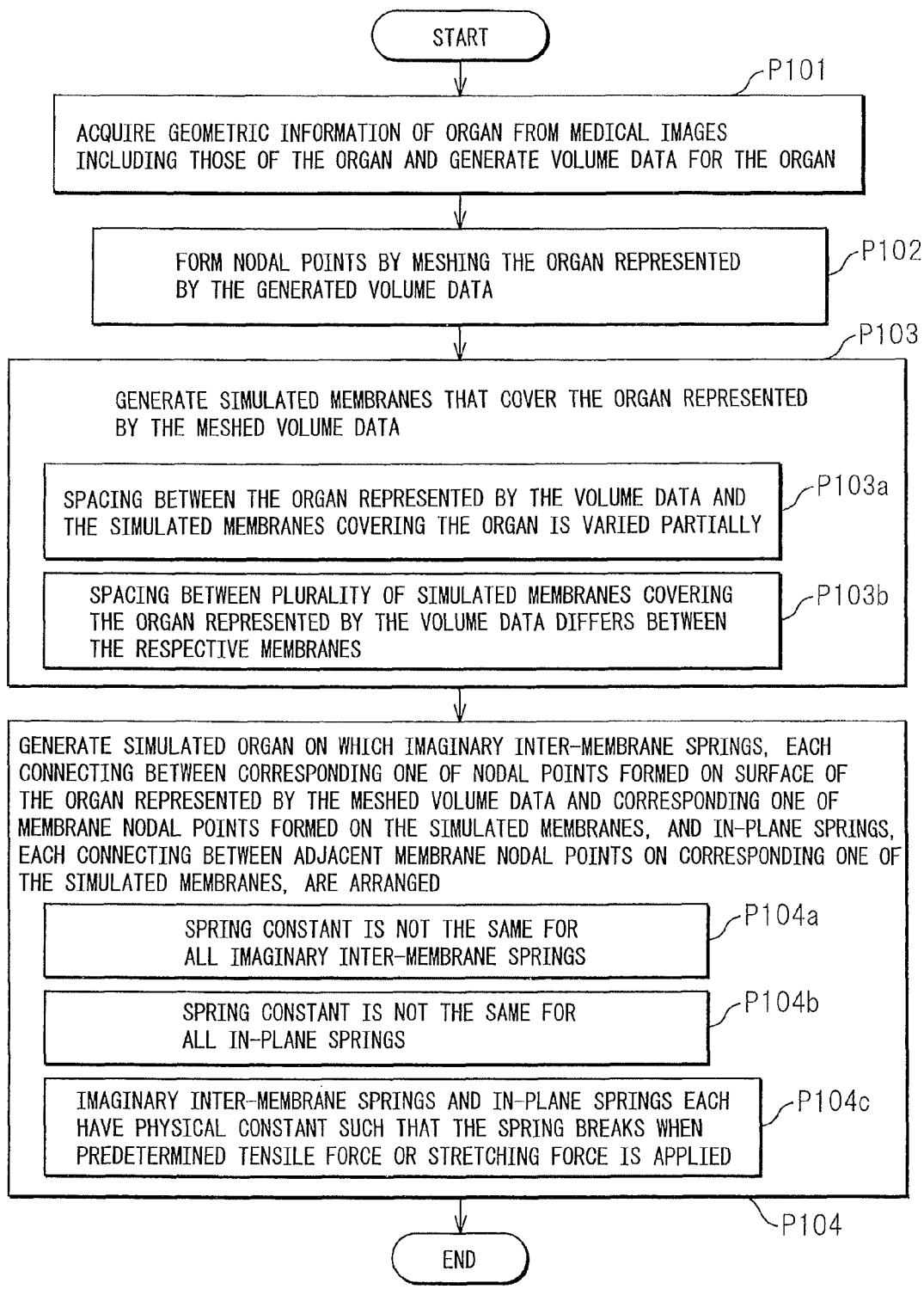
FIG. 1 is a flow diagram for explaining a first embodiment of a surgical simulation model generating method.
Figure 2:
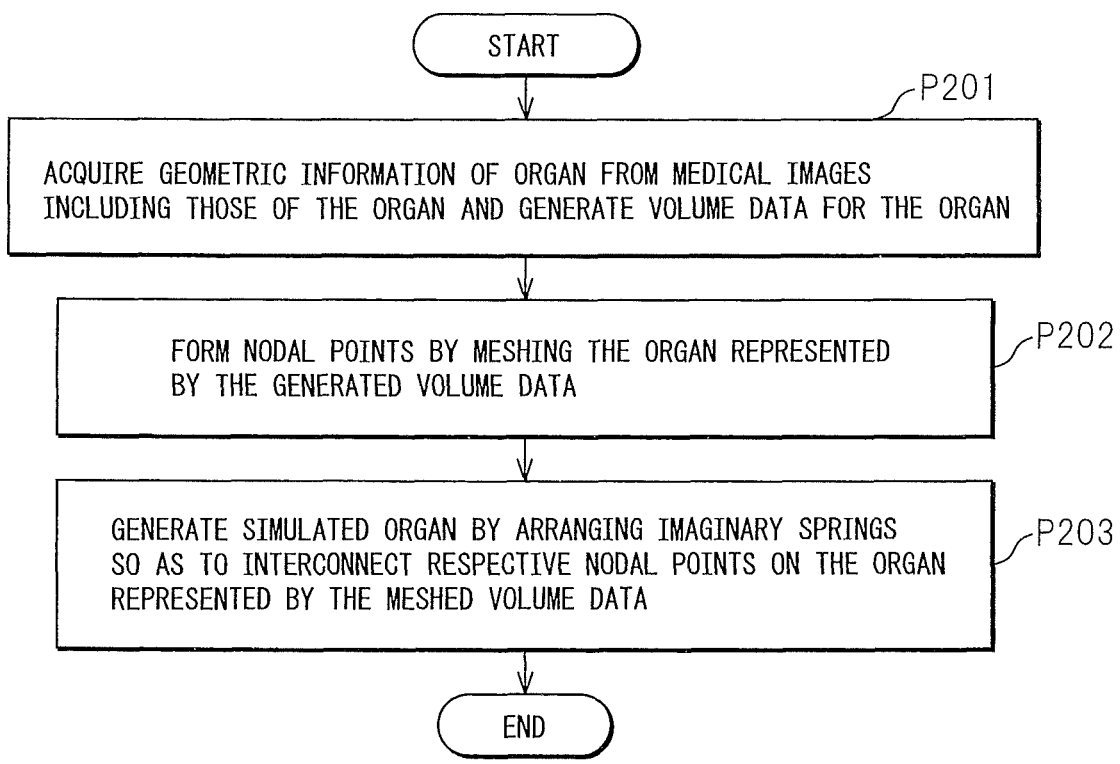
FIG. 2 is a flow diagram for explaining a second embodiment of a surgical simulation model generating method.
Figure 3:
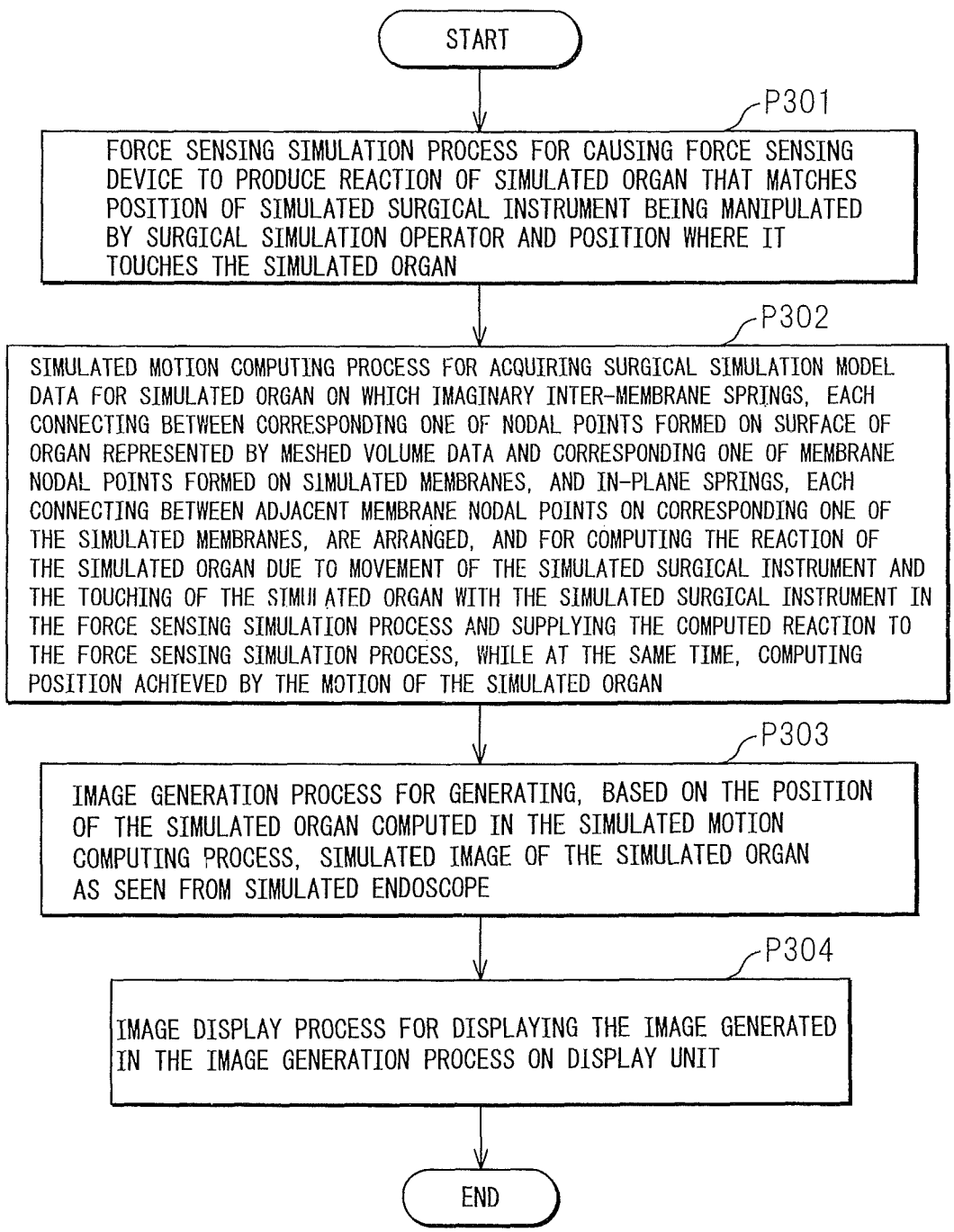
FIG. 3 is a flow diagram for explaining a first embodiment of a surgical simulation method.
Figure 5B:
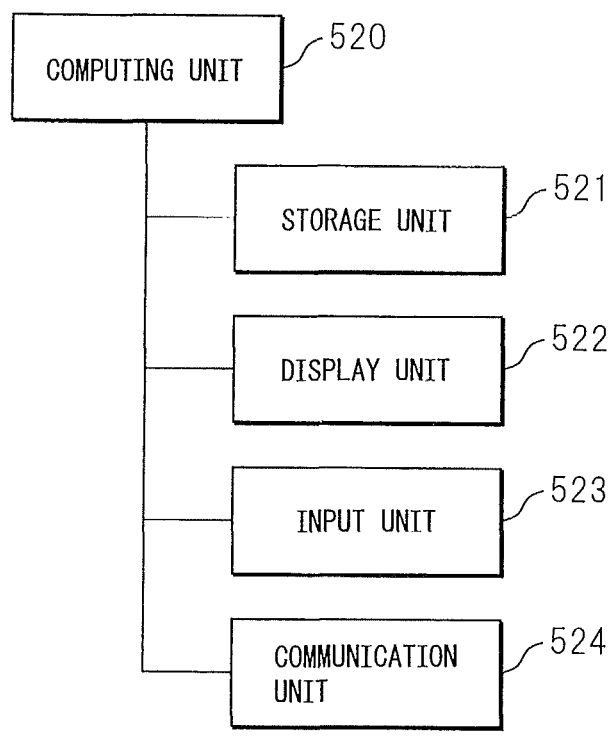
FIG. 5B is a functional block diagram of a computer.

FIG. 1 is a flow diagram for explaining a first embodiment of a surgical simulation model generating method. FIG. 2 is a flow diagram for explaining a second embodiment of a surgical simulation model generating method. FIG. 3 is a flow diagram for explaining a first embodiment of a surgical simulation method. FIG. 4 is a flow diagram for explaining a second embodiment of a surgical simulation method. FIG. 5A is a functional block diagram for explaining an embodiment of a surgical simulator. FIG. 5B is a functional block diagram of a computer.

In FIG. 5A, reference numeral 501 is a medical image data storage unit, 502 is a volume data constructing unit, 503 is an image generating unit, 504 is an image display device, 505 is a surgical simulation model data unit, 506 is a force sensing device, 507 is a simulated motion computing unit, 203 is a simulated surgical instrument, 509 is a simulated endoscope, and 510 is a simulated forceps. The simulated surgical instrument 203 includes the simulated surgical instrument 203 and the simulated endoscope 509.

FIG. 5B is a functional block diagram of a computer which implements some of the functions shown in FIG. 5A. The computer includes a computing unit 520, a storage unit 521, a display unit 522, an input unit 523, and a communication unit 534. The surgical simulation model generating method and the surgical simulation method are each realized by the computer executing a prescribed program. Further, the functions of the surgical simulator shown in FIG. 5A, except the functions of the force sensing device 506 and the simulated surgical instrument 203, are implemented by the computer executing a prescribed program. Here, the computing unit 520 controls the force sensing device 506 and the simulated surgical instrument 203 by performing communications with them using the communication unit 534. The image display device 504 is realized by the display unit 522.

Embodiment 1

The first embodiment of the surgical simulation model generating method will be described below. The surgical simulation model generation according to the first embodiment is performed using the surgical simulator shown in FIG. 5A.

The medical image data storage unit 501 stores the source data of medical images including, for example, those of the organ to be operated on. The source data of medical images is obtained, for example, by CT imaging or MRI imaging.

The image generating unit 503 generates images, including those of organs, by using the medical image data stored in the medical image data storage unit 501. The images, each representing a cross section of the patient to be operated on, are obtained by scanning the patient's body in thin slices in a prescribed direction. The volume data constructing unit 502 acquires geometrical information of each organ from the medical image data obtained by capturing the images of body parts, including those of the organ, while viewing the medical images, including those of the organ, displayed on the image display device 504. Then, based on the geometrical information of each organ thus acquired, the volume data constructing unit 502 extracts each body part (organ) two-dimensionally from the medical image data, and generates images by arranging the two-dimensionally extracted body parts in accordance with their predetermined positions relative to each other. Further, the volume data constructing unit 502 constructs three-dimensional volume data of each body part (P101 in FIG. 1) by stacking one on top of another the two-dimensional images of each body part extracted from the images of the thin slices. The three-dimensional volume data is stored in the medical image data storage unit 501 in a storage area different from the storage area where the source data of the medical images is stored. The volume data of each organ can be generated using, for example, a prior known method.

The operator of the surgical simulator causes the image generating unit 503 to retrieve from the medical image data storage unit 501 the medical image data of the patient to be operated on. The image generating unit 503 extracts the organs situated in the predetermined area containing the intended organ for which the data has been retrieved, and displays them on the image display device 504 in accordance with their predetermined positions relative to each other.

The operator reorients the intended organ by moving and/or rotating the volume data of the intended organ, as needed, by selecting it from among the organs displayed on the image display device 504. This is done so that the orientation of the organ based on the volume data matches the orientation of the organ as seen from an endoscope in actual surgery.

The volume data has an ID assigned to each organ. The ID of the original volume data before the move/rotate is designated as ID=F(x,y,z), and the volume data after the move/rotate as ID=G(x,r,z). When this move/rotate transformation is expressed in the form of a matrix $R_{ID}$, the relationship between F and G is given as $R_{ID}F=G$, so that G can be obtained as $G=R_{ID}^{-1}F$. The moved position data, including the matrix $R_{ID}$, is stored in the surgical simulation model data unit 505.

Next, as the intended organoved as described above, the volume data and the moved position data are also generated for other organs connected to the intended organ. The model data, etc., for these other organs are also stored in the surgical simulation model data unit 505.

Then, for each organ represented by the volume data, the volume data constructing unit 502 takes the geometrical information such as mesh spacing as input information, and generates, using a program, a finite-element model of the organ by meshing the volume data with tetrahedrons and thus forming nodal points thereon based on its anatomical properties (P102 in FIG. 1).

Next, for the organ represented by the volume data, the volume data constructing unit 502 takes the geometrical information such as mesh spacing as input information, and generates, based on the anatomical properties, a plurality of simulated membranes around the organ represented by the designated volume data (P103 in FIG. 1). The spacing from one simulated membrane to another is determined based on the thicknesses of the simulated membranes generated. The spacing between the organ represented by the volume data and the simulated membranes covering the organ may be constant or may be varied partially. Further, the spacing between the plurality of simulated membranes covering the organ represented by the volume data may be made the same or may be made different between the respective membranes (P103a and P103b in FIG. 1). In this way, a model that can variously change the deformation of the simulated membranes can be generated.

Figure 6:
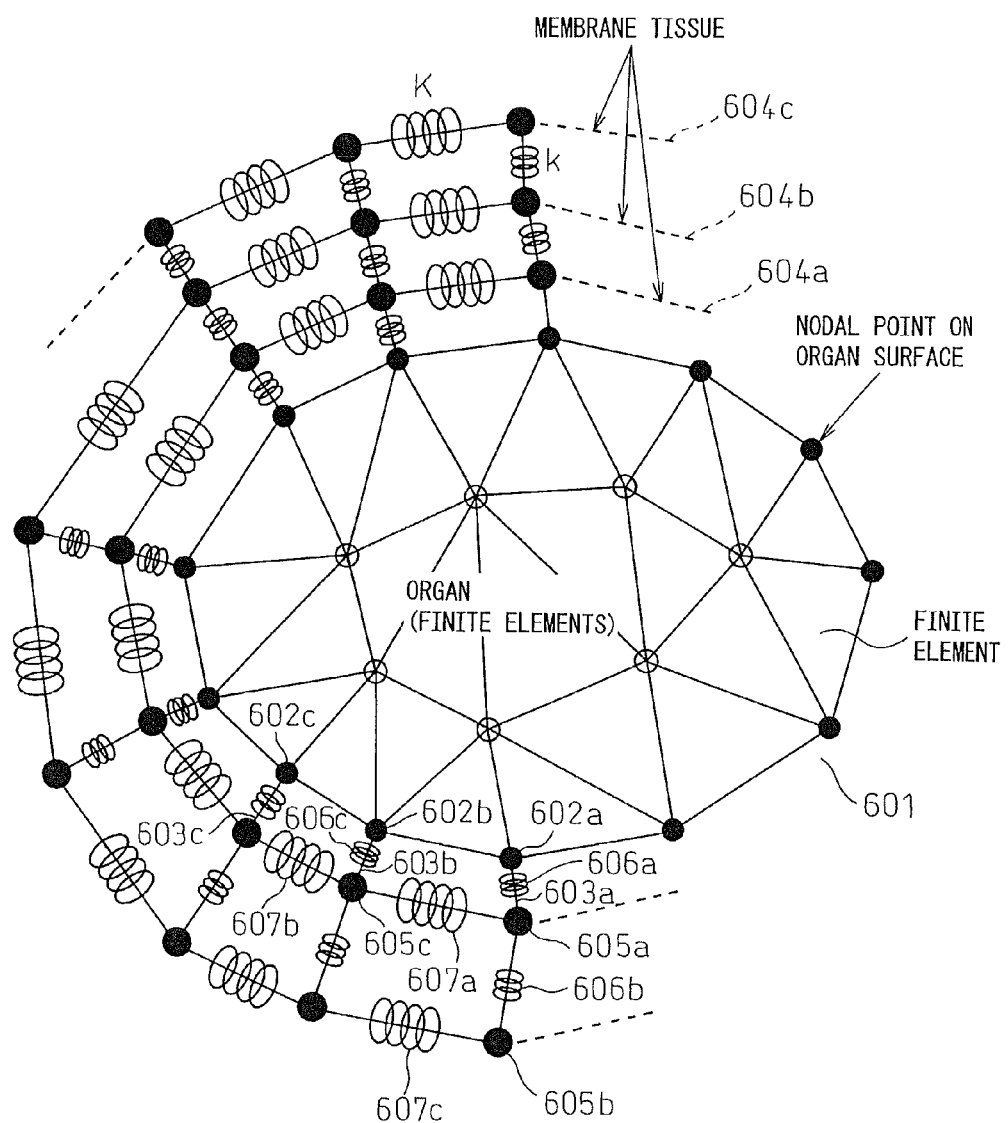
FIG. 6 is a diagram for explaining the structure of a membrane.

More specifically, as shown in FIG. 6, the volume data constructing unit 502 draws imaginary lines 603a, 603b, 603c, . . . so as to extend from the nodal points 602a, 602b, 602c, . . . formed on the surface of the organ 601 represented by the volume data meshed in process P102, in directions that intersect the simulated membranes 604a, 604b, 604c, . . . . Each imaginary line extends in a direction normal to the simulated membranes.

Then, the volume data constructing unit 502 forms membrane nodal points 605a, 605b, 605c, . . . at the points where the imaginary lines 603a, 603b, 603c, . . . intersect the simulated membranes 604a, 604b, 604c, . . . generated in process P103. Each imaginary line intersects the plurality of simulated membranes, and the membrane nodal points are formed one at each intersection.

Then, the volume data constructing unit 502 arranges, on each of the imaginary lines 603a, 603b, 603c, . . . , imaginary inter-membrane springs 606a, 606b, 606c, . . . that connect between a corresponding one of the nodal points 602a, 602b, 602c, . . . formed on the surface of the organ and a corresponding one of the membrane nodal points 605a, 605b, 605c, . . . and between the corresponding membrane nodal points on any two adjacent simulated membranes (P104 in FIG. 1).

Further, the volume data constructing unit 502 arranges in-plane springs 607a, 607b, 607c, . . . each connecting between adjacent membrane nodal points on a corresponding one of the simulated membranes (P104 in FIG. 1). In this way, a simulated organ having the organ represented by the meshed volume data and the simulated membranes covering the organ represented by the meshed volume data is generated.

The imaginary inter-membrane springs 606a, 606b, 606c, . . . and the in-plane springs 607a, 607b, 607c, . . . are each formed using a spring model.

More specifically, the imaginary inter-membrane springs 606a, 606b, 606c, . . . arranged between the respective nodal points formed on the surface of the organ may be chosen to have different spring constants k (k=k1, k2, . . . ), and the in-plane springs 607a, 607b, 607c, . . . may also be chosen to have different spring constants K (K=K1, K2, . . . ) (P104a and P104b in FIG. 1). Alternatively, all of the spring constants k or all of the spring constants K may be made the same. In this way, when force is applied to the simulated membranes, the corresponding portions of the simulated membranes do not deform uniformly along the imaginary line direction but deform differently according to the different spring constants. Further, when force is applied to the simulated membranes, each simulated membrane does not deform uniformly in the plane but deforms differently according to the different spring constants. The values of the spring constants k and K can be set based, for example, on anatomical data.

Furthermore, the imaginary inter-membrane springs 606a, 606b, 606c, . . . and the in-plane springs 607a, 607b, 607c, . . . may each has a physical constant such that the spring breaks when a predetermined tensile force or stretching force is applied (P104c in FIG. 1). This simulates the simulated membrane being torn off when a force is applied to the simulated membrane. This physical constant can be set based, for example, on anatomical data.

Then, the volume data constructing unit 502 stores the surgical simulation model data for such a simulated organ into the surgical simulation model data unit 505.

According to the surgical simulation model generating method of the first embodiment described above, since the simulation accuracy of membrane deformation can be improved with the spring forces acting in the plane of each simulated membrane, a model is generated that makes it possible to achieve a surgical simulation having a high training effect.

Embodiment 2

Next, a method for generating a surgical simulation model intended to simulate a large deformation of a designated organ with high accuracy will be described below with reference to FIG. 2. The surgical simulation model generation according to the second embodiment also is performed using the surgical simulator shown in FIG. 5A.

In FIG. 2, processes P201 and P202 are the same as the corresponding processes P101 and P102 shown in FIG. 1.

Figure 7:
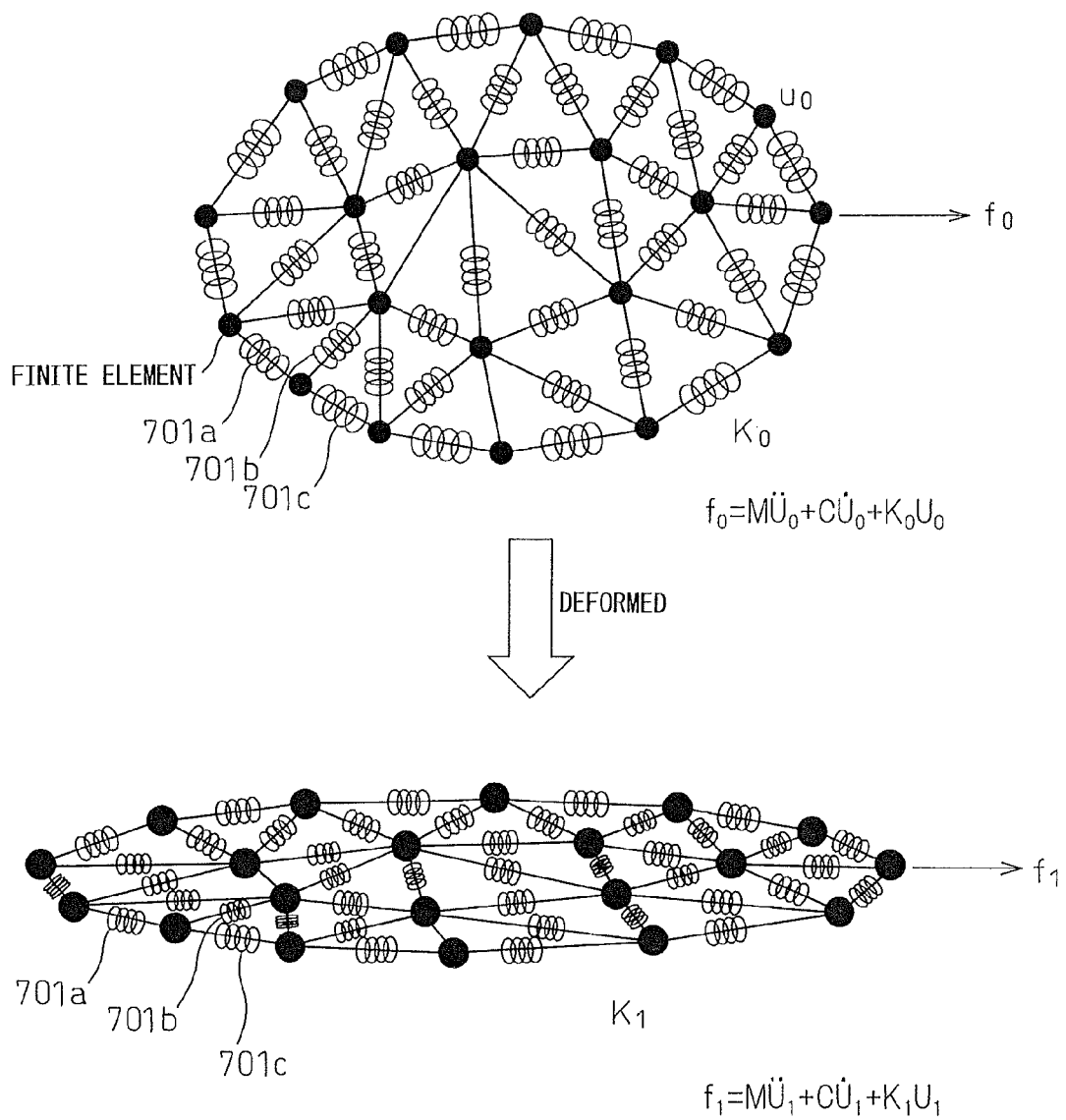
FIG. 7 is a diagram for explaining a finite-element model of an organ.

Next, in process P203, the volume data constructing unit 502 generates a simulated organ by arranging imaginary springs 701a, 701b, 701c, . . . so as to interconnect the respective nodal points on the finite-element model of the organ represented by the volume data meshed with tetrahedrons (FIG. 7). Each imaginary spring is arranged between adjacent nodal points on the organ represented by the volume data.

The imaginary springs 701a, 701b, 701c, . . . are each formed using a spring model. The imaginary springs are arranged between the respective nodal points on the surface of the organ and between the respective nodal points inside the organ. As in the first embodiment, the imaginary springs may include those having different spring constants. The spring constants of the imaginary springs can be set based, for example, on anatomical data.

Figure 8:
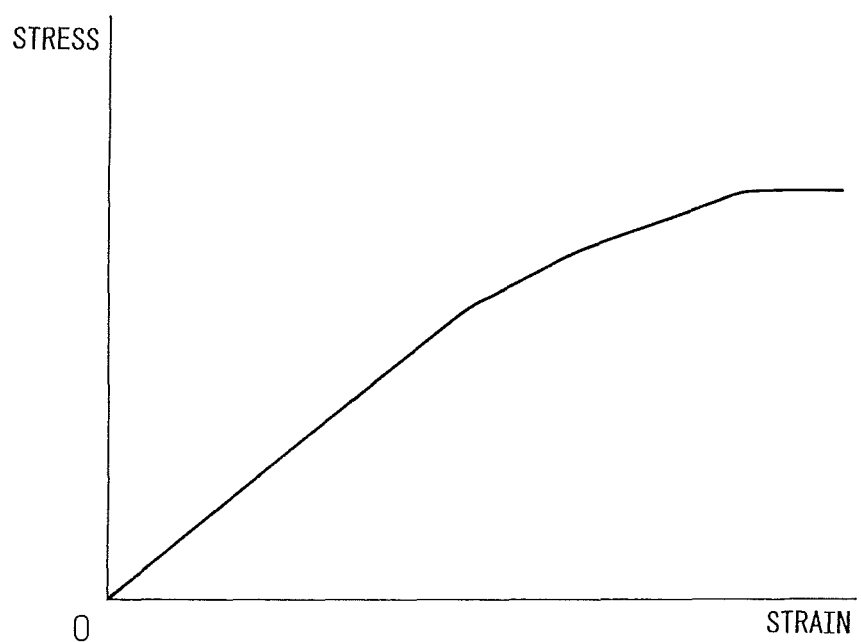
FIG. 8 is a diagram for explaining the characteristic of an imaginary spring.

Further, the imaginary springs 701a, 701b, 701c, . . . may each has a physical constant such that the spring breaks when a prescribed tensile force or stretching force is applied. In this case, the imaginary springs 701a, 701b, 701c, . . . may each has a characteristic that is not linear with respect to the applied tensile force or stretching force. For example, each imaginary spring may have a nonlinear characteristic that is convex upward as shown in FIG. 8, and may be constructed to break when the prescribed tensile force or stretching force is applied. The nonlinear physical characteristics of the imaginary springs can be set based, for example, on anatomical data.

In this way, the simulated organ is generated by arranging the imaginary springs so as to interconnect the respective nodal points formed by meshing the organ represented by the volume data.

Then, the volume data constructing unit 502 stores the surgical simulation model data for such a simulated organ into the surgical simulation model data unit 505.

According to the surgical simulation model generating method of the second embodiment described above, since the simulation accuracy of simulated organ deformation can be improved with the spring forces acting on the simulated organ, a model is generated that makes it possible to achieve a surgical simulation having a high training effect.

Embodiment 3

Next, a description will be given of a surgical simulation that uses the surgical simulation model data generated according to the first embodiment and an apparatus that is used to perform the simulation. The surgical simulation according to the third embodiment is performed using the surgical simulator shown in FIG. 5A.

The image generating unit 503 retrieves from the surgical simulation model data unit 505 the surgical simulation model data for the simulated organ having the organ represented by the meshed volume data and the simulated membranes covering the organ represented by the meshed volume data. Then, the image generating unit 503 causes the image display device 504 to display the simulated organ having the simulated organ and the plurality of simulated membranes arranged around the organ. In this simulated organ, the imaginary inter-membrane springs and the in-plane springs are arranged as earlier described, defining the dynamic properties of the simulated organ.

The surgical simulation operator of the surgical simulator touches a simulated membrane forming part of the simulated organ by manipulating the simulated forceps 510 as one of the simulated surgical instruments 203, and pulls the simulated membrane by holding it between the pincers of the simulated forceps 510. The reaction of the simulated organ that matches the position of the simulated forceps 510 and the position where it touches the simulated membrane is produced by the force sensing device 506, and this reaction is fed back to the simulated forceps 510 through the force sensing device 506 (P301). As the force sensing device 506, use may be made, for example, of a prior known force sensing device.

To produce the reaction of the simulated organ, the simulated motion computing unit 507 acquires the surgical simulation model data for the simulated organ from the surgical simulation model data unit 505, and computes the reaction of the simulated organ due to the movement of the simulated forceps 510 and the touching of the simulated organ with the simulated forceps 510 at the force sensing device 506 (P302). Further, the simulated motion computing unit 507 supplies the thus computed reaction to the force sensing device 506, while at the same time, computing the position achieved by the motion of the simulated organ (P302).

More specifically, the reaction to be applied to the simulated forceps 510 is computed by the simulated motion computing unit 507, based on the spring constants of the imaginary inter-membrane springs 606a, 606b, 606c, . . . and in-plane springs 607a, 607b, 607c, . . . and on the moved position of the simulated forceps 510. The simulated motion computing unit 507 causes the force sensing device 506 to produce the computed reaction as a tensile force, and the reaction is thus simulated. The gripping force exerted by the simulated forceps differs depending on the position of the pincers of the simulated forceps 510, and this gripping force is computed by the simulated motion computing unit 507. When the stretching or tensile force with which the simulated membrane is being pulled by the simulated forceps 510 reaches or exceeds a predetermined value, the imaginary inter-membrane springs 606a, 606b, 606c, . . . and the in-plane springs 607a, 607b, 607c, . . . are caused to break, thus simulating the simulated membrane being torn off (P302). In this way, when the simulated forceps is pulled with a predetermined tensile force or stretching force, the imaginary inter-membrane springs or the in-plane springs are caused to break, thus applying the sensation of tearing off the simulated membrane to the simulated forceps. The surgical simulator can thus simulate the simulated membrane being torn off when a force is applied to it.

Preferably, the simulated motion computing unit 507 performs the above computations in real time in the surgical simulation. The real time computing method of the simulated motion computing unit 507 is the same as the method to be described later as a fourth embodiment, and will therefore be described in detail later. Further, to enhance the computational speed, the simulated motion computing unit 507 may be implemented using a computer different from the computer used to implement the other functions. Performing the surgical simulation in real time means performing the surgical simulation at about the same speed as the actual surgery will be performed.

During the surgical simulation, the image generating unit 503 generates simulated images of the simulated organ and simulated membranes as seen from the simulated endoscope, based on the positions of the simulated organ and simulated membranes computed by the simulated motion computing unit 507. In this way, the image generating unit 503 generates dynamically simulated images of the simulated organ and the simulated surgical instructions 203 including the simulated forceps, as if the images were being actually captured by the simulated endoscope (P303). As the image generating unit 503, use may be made, for example, of a prior known image generating unit.

The simulated images are displayed on the image display device 504, and the surgical simulation operator performs the surgical simulation while viewing the displayed images (P304).

According to the surgical simulation method and surgical simulator of the third embodiment described above, the motion of each simulated membrane can be computed in real time. Further, since the simulation accuracy of membrane deformation can be improved with the spring forces acting in the plane of each simulated membrane, a surgical simulation having a high training effect can be achieved. Furthermore, since the simulation accuracy of simulated organ deformation can be improved in the simulation of a large deformation of the simulated organ, a surgical simulation having a high training effect can be achieved. Moreover, since the tensile force exerted when the simulated membrane is pulled is fed back to the simulated forceps through the force sensing device, a simulation with enhanced reality can be achieved.

Embodiment 4

Next, a description will be given of a surgical simulation that uses the surgical simulation model data generated according to the second embodiment and an apparatus that is used to perform the simulation. The surgical simulation according to the fourth embodiment is performed using the surgical simulator shown in FIG. 5A.

The image generating unit 503 acquires from the surgical simulation model data unit 505 the surgical simulation model data for the simulated organ generated by arranging the imaginary springs so as to interconnect the respective nodal points formed by meshing the organ represented by the volume data. Then, the image generating unit 503 generates images of the simulated organ including the simulated organ, and displays them on the image display device 504.

The surgical simulation operator of the surgical simulator touches the simulated organ forming part of the simulated organ by manipulating the simulated forceps 510 as one of the simulated surgical instruments 508, and pushes or pulls the simulated organ by holding it between the pincers of the simulated forceps 510. The reaction that matches the position of the simulated forceps 510 and the position where it touches the simulated organ is produced by the force sensing device 506 (P401).

To produce the reaction of the simulated organ, the simulated motion computing unit 507 acquires the surgical simulation model data for the simulated organ from the surgical simulation model data unit 505, and computes the reaction of the simulated organ due to the movement of the simulated surgical instrument and the touching of the simulated organ with the simulated surgical instrument at the force sensing device 506 (P402). Further, the simulated motion computing unit 507 supplies the thus computed reaction to the force sensing device 506, while at the same time, computing the position achieved by the motion of the simulated organ (P402).

More specifically, the reaction to be applied to the simulated forceps 510 is computed by the simulated motion computing unit 507, based on the nonlinear spring constants of the imaginary springs 701a, 701b, 701c, . . . and on the moved position of the simulated forceps. The simulated motion computing unit 507 causes the force sensing device 506 to produce the computed reaction as a compression or tensile force, and the reaction is thus simulated. The gripping force exerted by the simulated forceps differs depending on the position of the pincers of the simulated forceps, and this gripping force is computed by the simulated motion computing unit 507.

A nonlinear FEM (Finite-Element Method) is used to generate an organ deformation model in order to simulate the deformation of the simulated organ with high accuracy.

The nonlinear process is performed in real time by piecewise linearizing the time evolution of the nonlinear process. In the prior art linear computation model, denoting the displacement vector as $<U>$, the mass matrix as $<M>$, the viscosity resistance matrix as $<C>$, the stiffness matrix $<K>$, and the external force $<f>$, and assuming that the displacement is small, the motion equation is defined by the following equation (1). (In this specification, the notation $<a>$ denotes a vector or matrix of "a", and is shown in boldface.)

$$M\ddot{U}+C\dot{U}+K(U)=f \quad (1)$$

In the fourth embodiment, the stiffness matrix K in equation (1) describes the physical values of the simulated organ and is generated using the spring constants of the imaginary springs. In the prior art simulated organ, the stiffness matrix was generated by using, for example, the physical values applied to the tetrahedrons of the finite-element mode. Further, in the fourth embodiment, the stiffness matrix $<K>$ is given as the following nonlinear model $<K(<U>)>$ which is a function of the displacement matrix $<U>$.

$$M\ddot{U}+C\dot{U}+K_f(U)=f \quad (2)$$
$$K_f(U)=\int_0^U K(u)du$$

When the stiffness matrix $<K>$ is given as $<K(<U>)>$, i.e., as a function of the displacement matrix $<U>$, the reaction of the simulated organ can be computed based on the physical values of the simulated organ obtained by varying the physical values according to the positional displacement of the simulated organ caused by the force applied to the simulated organ. In this way, since the simulation accuracy of simulated organ deformation can be improved in the simulation of a large deformation of the simulated organ, a surgical simulation having a high training effect can be achieved.

(Piecewise Linearization)

IF force is applied to an object (for example, the simulated organ) by using a simulated surgical instrument such as a simulated forceps, the object is deformed, generating stress; then, the deformation of the object ceases when the surface force of the object equilibrates with the force exerted by the simulated surgical instrument, and the equilibrium of the forces is thus reached. When the force is further applied, the object is further deformed until the surface force is generated to equilibrate with it and, when the equilibrium of the forces is reached, the deformation is stabilized. In real time processing, this process is repeated at high speed.

When such dynamic computations are assumed, it is considered that the difference between the stiffness matrix one frame back in time (stress-generating source information) and the current stiffness matrix is small (i.e., piecewise linearized). In particular, in the case of the surgical simulator, the operation is relatively mild. Hence, using the stiffness matrix $<K_f>_i$ corresponding to the position ($<U>^{k-1}$) one frame back in time and the amount of displacement, $\Delta<u>^k_i$, during one frame, the following equation (3) is obtained.

$$K_{fi}(u_i^k)=K_{fi}(u_i^{k-1})+K_{fi}(u_i^{k-1})\cdot \Delta u_i^{k-1} \quad (3)$$

Accordingly, the process proceeds as follows:

(1) $K_{fi}(u_i^k)=K_{fi}(u_i^{k-1})+K_{fi}(u_i^{k-1})\cdot \Delta u_i^{k-1}$ (2) $\alpha hd\ i^k=(f_i^k-C_i\cdot v_i^{k-1}-K_{fi}(u_i^k))/M_i$ (3) $v_i^k=v_i^{k-1}+\alpha_i^k \Delta t$ (4) $\Delta u_i^{k-1}=v_i^k \Delta t$ (5) $u_i^k=u_i^{k-1}+\Delta u_i^k$ (6) $K_{fi}^k$ is calculated using $u_i^k$.

(7) The process returns to (1) (until $i=N$). (4)

Figure 9:
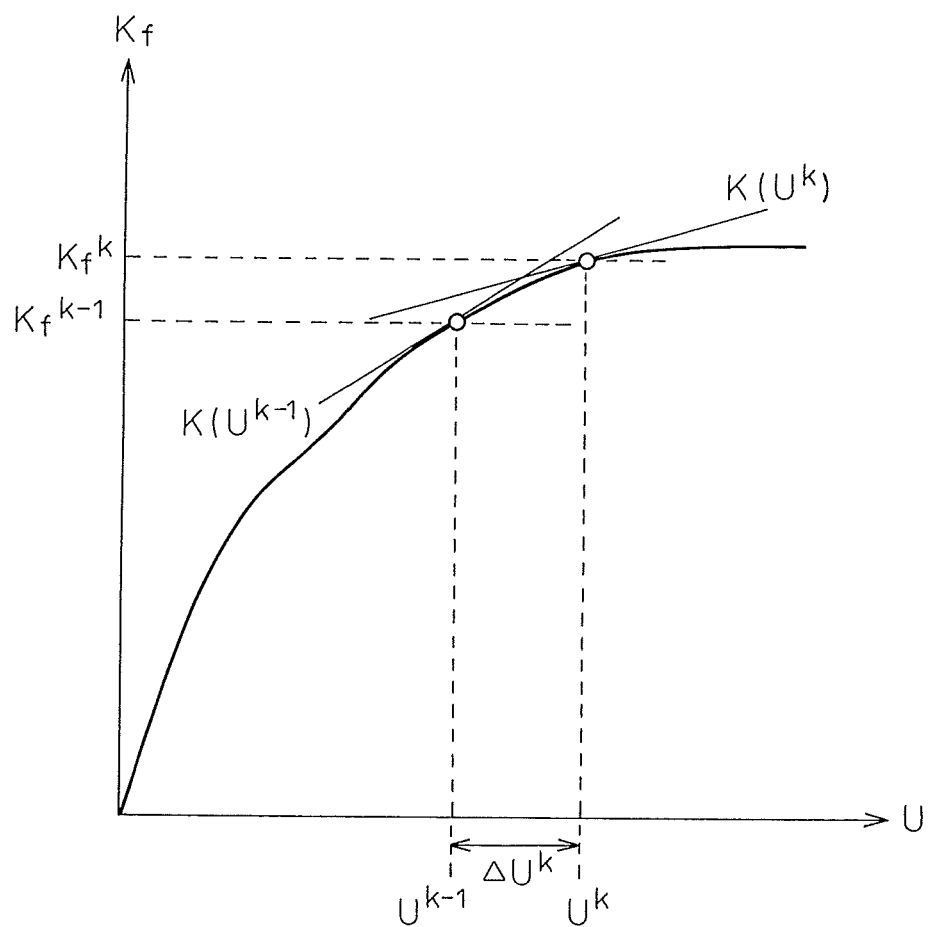
FIG. 9 is a diagram showing the relationship between $<K_f>$, $<K(<U>)>$, and $<U>$.

The entire process from (1) to (7) forms equation (4). The superscript k represents the computation time instant, $\alpha_i$ represents the acceleration of the i-th element, $f_i$ represents the external force of the same, $v_i$ represents the velocity of the same, $u_i$ represents the displacement of the same, and $K_{fi}$ represents the stiffness force. FIG. 9 shows the relationship between $<K_f>$, $<K(<U>)>$, and $<U>$. Further, $<U^k>$ represents a stack of $u_i^k$ corresponding to the respective elements and is written as $$u^k=(u_1^k,u_2^k,\ldots,u_N^k) \quad (5)$$

where N represents the number of finite elements.

To calculate $K_{fi}^k$ using $u_i^k$ in the above process (6), $K_{fi}$ is denoted as $K_e$, and the following equation (6) is solved.

$$Ke=\int B(x)^T DB(x)dx_1 dx_2 dx_3 \quad (6)$$

Here, $<B(<x>)>$ is a shape matrix that relates the strain tensor to the displacement (displacement from nodal point 1 to nodal point n) by the equation (strain tensor)=(shape matrix)·(displacement), and $<D>$ is a property matrix that relates the stress tensor to the strain tensor by the equation (stress tensor)=(property matrix)·(strain tensor).

Further, each $u_m$ in $u^k=(u_1^k, u_2^k, \ldots, u_N^k)$ is described as $u_m=((x1, x2, x3)_{p(m)}, (x1, x2, x3)_{q(m)}, (x1, x2, x3)_{r(m)}, (x1, x2, x3)_{s(m)})$, [m: 1, 2, . . . , N]. Here, m represents the element number, and indicates that the total number of elements is N. On the other hand, p(m), q(m), r(m), and s(m) indicate the numbers of the four nodal points forming the element m as a tetrahedron. Further, $(x1, x2, x3)_{p(m)}$ represents the displacement at the nodal point p(m).

By processing the above equation (4), the simulated motion computing unit 507 reconfigures the stiffness matrix $<K>$ according to the shape and updates it on a frame-by-frame basis on the simulated motion computing unit 507 (P402).

In the fourth embodiment, since the stiffness matrix K is generated using the spring constants of the imaginary springs, the matrix elements are simple in configuration. Accordingly, the simulated motion computing unit 507 can perform the computation of equation (4) using the stiffness matrix K at high speed. While the computation using the prior art stiffness matrix has had the problem that the computation may diverge, in the fourth embodiment the computation of equation (4) does not diverge but converges because the stiffness matrix K is formed from matrix elements of simple configuration.

During the surgical simulation, the image generating unit 503 generates simulated images of the simulated organ as seen from the simulated endoscope, based on the position of the simulated organ computed by the simulated motion computing unit 507. In this way, the image generating unit 503 generates motion simulated images of the simulated organ and the simulated surgical instructions 203 including the simulated forceps, as if the images were being actually captured by the simulated endoscope (P403).

The image generating unit 503 displays the simulated images on the image display device 504, and the surgical simulation operator performs the surgical simulation while viewing the displayed images (P404).

According to the surgical simulation method and surgical simulator of the fourth embodiment described above, the position achieved by the motion of the simulated organ can be computed in real time. Further, since the simulation accuracy of simulated organ deformation can be improved with the spring forces acting on the simulated organ, a surgical simulation having a high training effect can be achieved.

In the earlier described third embodiment, the stiffness matrix K describes the physical values of the simulated organ and is generated using the spring constants of the imaginary inter-membrane springs and in-plane springs. Then, the motion of the simulated membranes is computed in real time by using the stiffness matrix K. In the third embodiment, the simulated organ may be constructed by using imaginary springs similar to those used to construct the simulated organ in the fourth embodiment.

DESCRIPTION OF THE REFERENCE NUMERALS

501: MEDICAL IMAGE DATA STORAGE UNIT, 502: VOLUME DATA CONSTRUCTING UNIT, 503: IMAGE GENERATING UNIT, 504: IMAGE DISPLAY DEVICE 505: SURGICAL SIMULATION MODEL DATA UNIT, 506: FORCE SENSING DEVICE, 507: SIMULATED MOTION COMPUTING UNIT, 508: SIMULATED SURGICAL INSTRUMENT, 509: SIMULATED ENDOSCOPE, 510: SIMULATED FORCEPS, 601: ORGAN, 602a, 602b, 602c, . . . : SURFACE NODAL POINTS, 603a, 603b, 603c, . . . : IMAGINARY LINES, 604a, 604b, 604c, . . . : SIMULATED MEMBRANES, 605a, 605b, 605c, . . . : MEMBRANE NODAL POINTS, 606a, 606b, 606c, . . . : IMAGINARY INTER-MEMBRANE SPRINGS, 607a, 607b, 607c, . . . : IN-PLANE SPRINGS.

What is claimed is:

1. A surgical simulation method comprising:
a force sensing simulation process in which a computing unit causes a force sensing device to produce reaction of a simulated organ that matches the position of a simulated surgical instrument being manipulated by a surgical simulation operator and the position where said simulated surgical instrument touches said simulated organ;
a simulated motion computing process in which said computing unit acquires, from a storage unit, surgical simulation model data for a simulated organ having an organ represented by meshed volume data and a simulated membrane covering said organ represented by said meshed volume data, said simulated organ being generated by drawing an imaginary line so as to extend from each nodal point formed on a surface of said organ represented by said meshed volume data in a direction that intersects said simulated membrane and thereby forming a membrane nodal point at a point where said imaginary line intersects said simulated membrane, and by arranging on each imaginary line an imaginary inter-membrane spring that connects between said nodal point formed on the surface of said organ and said membrane nodal point, while also arranging an in-plane spring that connects between adjacent membrane nodal points on said simulated membrane, and said computing unit then computes the reaction of said simulated organ due to a movement of said simulated surgical instrument and the touching of said simulated organ with said simulated surgical instrument in said force sensing simulation process, and supplies said computed reaction to said force sensing simulation process, while at the same time, computing the position achieved by the motion of said simulated organ;
an image generation process in which said computing unit generates, based on the position of said simulated organ computed in said simulated motion computing process, a simulated image of said simulated organ as seen from a simulated endoscope; and
an image display process in which said computing unit displays said image generated in said image generation process on a display unit,
wherein in said simulated motion computing process, said computing unit computes the reaction, f, of said simulated organ by using an equation $$M\ddot{U} + C\dot{U} + K_f(U) = f$$

$$K_f(U) = \int_0^U K(u)du$$

where displacement vector U represents a positional displacement of said simulated organ stiffness matrix $K_f$ represents a physical value of said simulated organ and is generated using spring constants of said imaginary inter-membrane spring and in-plane spring by integrating stiffness matrix K(u) which is given as a function of position vector u with respect to position vector u, matrix M is a mass matrix, and matrix C is a viscosity resistance matrix.

2. A surgical simulation method as claimed in claim 1, wherein in said surgical simulation model data, said simulated organ includes a plurality of simulated membranes generated so as to cover said organ represented by said meshed volume data, wherein each imaginary line intersects said plurality of simulated membranes, and wherein, on each imaginary line, imaginary inter-membrane springs are arranged that connect between a corresponding one of said nodal points formed on the surface of said organ represented by said meshed volume data and a corresponding one of said membrane nodal points and between corresponding membrane nodal points on any two adjacent simulated membranes.

3. A surgical simulator comprising:
a surgical simulation model data unit which stores surgical simulation model data for a simulated organ having an organ represented by meshed volume data and a simulated membrane covering said organ represented by said meshed volume data, said surgical simulation model data being generated by drawing an imaginary line so as to extend from each nodal point formed on a surface of said organ represented by said meshed volume data in a direction that intersects said simulated membrane and thereby forming a membrane nodal point at a point where said imaginary line intersects said simulated membrane, and by arranging on each imaginary line an imaginary inter-membrane spring that connects between said nodal point formed on the surface of said organ and said membrane nodal point, while also arranging an in-plane spring that connects between adjacent membrane nodal points on said simulated membrane;

a force sensing device which produces a reaction of said simulated organ that matches the position of a simulated surgical instrument being manipulated by a surgical simulation operator and the position where said simulated surgical instrument touches said simulated organ;

a simulated motion computing unit which acquires said surgical simulation model data from said surgical simulation model data unit, computes the reaction of said simulated organ due to a movement of said simulated surgical instrument and the touching of said simulated organ with said simulated surgical instrument at said force sensing device, and supplies said computed reaction to said force sensing device, while at the same time, computing the position achieved by the motion of said simulated organ;

an image generating unit which generates, based on the position of said simulated organ computed by said simulated motion computing unit, a simulated image of said simulated organ as seen from a simulated endoscope; and an image display unit which displays said image generated by said image generating unit, wherein said simulated motion computing unit computes the reaction, f, of said simulated organ by using an equation $$M\ddot{U} + C\dot{U} + K_f(U) = f$$

$$K_f(U) = \int_0^U K(u)du$$

where displacement vector U represents a positional displacement of said simulated organ stiffness matrix $K_f$ represents a physical value of said simulated organ and is generated using spring constants of said imaginary inter-membrane spring and in-plane spring by integrating stiffness matrix K(u) which is given as a function of position vector u with respect to position vector u, matrix M is a mass matrix, and matrix C is a viscosity resistance matrix.

4. A surgical simulator as claimed in claim 3, wherein in said surgical simulation model data, said simulated organ includes a plurality of simulated membranes generated so as to cover said organ represented by said meshed volume data, wherein each imaginary line intersects said plurality of simulated membranes, and wherein, on each imaginary line, imaginary inter-membrane springs are arranged that connect between a corresponding one of said nodal points formed on the surface of said organ represented by said meshed volume data and a corresponding one of said membrane nodal points and between corresponding membrane nodal points on any two adjacent simulated membranes.

* * * * *